United States Patent
Bender et al.

(10) Patent No.: US 7,262,314 B2
(45) Date of Patent: Aug. 28, 2007

(54) 3-IODOPROPYLMETHYLDIISO-PROPOXYSILANE AND IMAGING MEMBERS INCLUDING THE SAME

(75) Inventors: Timothy P. Bender, Port Credit (CA); Nan-Xing Hu, Oakville (CA)

(73) Assignee: Xerox Corporation, Stamford, CT (US)

( * ) Notice: Subject to any disclaimer, the term of this patent is extended or adjusted under 35 U.S.C. 154(b) by 492 days.

(21) Appl. No.: 10/886,146

(22) Filed: Jul. 7, 2004

(65) Prior Publication Data

US 2006/0009650 A1    Jan. 12, 2006

(51) Int. Cl.
*C07F 7/08* (2006.01)
(52) U.S. Cl. .................................... 556/478
(58) Field of Classification Search ............... None
See application file for complete search history.

(56) References Cited

U.S. PATENT DOCUMENTS

| 5,368,967 | A | 11/1994 | Schank et al. |
| 5,681,679 | A | 10/1997 | Schank et al. |
| 6,495,300 | B1 | 12/2002 | Qi et al. |

OTHER PUBLICATIONS

Nakao et al, (Synthesis and photochromic properties of spironaphth [1,2-b]oxazine containing a reactive substituent, Dyes and Pigments (2002), 52(2), 95-100).*

* cited by examiner

*Primary Examiner*—Samuel Barts
(74) *Attorney, Agent, or Firm*—Eugene O. Palazzo; Fay Sharpe LLP

(57) ABSTRACT

A method for preparation of an iodoalkylalkoxysilane includes contacting a haloalkylmethoxysilane with an alcohol in the presence of a protic acid to form a haloalkylalkoxysilane. The haloalkylalkoxysilane is contacted with an iodide to form the iodoalkylalkoxysilane. The iodoalkylalkoxysilane can be used as a chemical intermediate in the preparation of functional aryl amine molecules which have application in the formation of thin films for photoreceptors.

20 Claims, 3 Drawing Sheets

3-IODOPROPYLMETHYLDIISO-PROPOXYSILANE AND IMAGING MEMBERS INCLUDING THE SAME

BACKGROUND

The present disclosure relates to a method for preparation of alkoxysilanes. It finds particular application in conjunction with the preparation of 3-iodopropylmethyidiisopropoxysilane and imaging members incorporating the same, and will be described with specific reference thereto. However, it is to be appreciated that the present disclosure is also amenable to other like applications.

Photoreceptor devices having a multilayer organic photoconductor coating (OPC) have been formed with a silicon-containing overcoat which increases the mechanical lifetime of the OPC. An exemplary patent directed to a photoconductive imaging member is U.S. Pat. No. 6,495,300 (Qi, et al.), which is incorporated herein by reference in its entirety. The imaging member disclosed comprises a supporting substrate, a photogenerating layer, a charge transport layer, and an overcoat consisting of a crosslinked composite polysiloxane-silica. The overcoat may be derived by crosslinking a trialkoxysilyl-functionalized hydroxyalkyl acrylate or trialkoxysilyl-functionalized hydroxyalkyl alkacrylate with an aminoalkylalkoxysilane, such as gamma-aminoalkyltrialkyloxysilane, and dispersing silica particles therein.

U.S. Pat. No. 5,681,679 (Schank, et al.), which is incorporated herein by reference in its entirety, discloses a flexible electrophotographic imaging member including a supporting substrate and a resilient combination of a photoconductive layer and an overcoating layer, the photoconductive layer comprising a hole transporting arylamine siloxane polymer and the overcoating comprising a crosslinked polyamide doped with a dihydroxy amine.

U.S. Pat. No. 5,368,967 (Schank et. al.), which is incorporated herein by reference in its entirety, discloses an electrophotographic imaging member comprising a substrate, a charge generating layer, a charge transport layer, and an overcoat layer comprising a small molecule hole transporting arylamine having at least two hydroxy functional groups, a hydroxy or multihydroxy triphenyl methane, and a polyamide film forming binder capable of forming hydrogen bonds with the hydroxy functional groups of the hydroxy arylamine and the hydroxy or multihydroxy triphenyl methane.

Recently, overcoat layers comprising siloxane and aromatic segments which include a triarylamine hole transport molecule have been produced. Such triarylamine molecules are prepared by reaction of carbonic acid salt groups on a triaryl amine precursor molecule with 3-iodopropylmethyldiisopropoxysilane by elimination of the iodide salt. The 3-iodopropylmethyldiisopropoxysilane is formed by reaction of 3-chloropropylmethyidimethoxysilane with a large excess of isopropyl alcohol in the presence of a protic acid catalyst (such as paratoluenesulphonic acid or anhydrous hydrochloric acid) with fractional distillation to remove the produced methyl alcohol as a mixture with excess isopropyl alcohol. Further reaction of this intermediate with iodide salts (such as potassium and sodium salts) under traditional Finklestein conditions affords 3-iodopropylmethyldiisopropoxysilane.

Accordingly, a need exists for producing 3-iodopropylmethyldiisopropoxy-silane and/or imaging members incorporating the same.

BRIEF DESCRIPTION

In accordance with one aspect of the present exemplary embodiment, a method for preparation of an iodoalkylalkoxysilane is provided. The method includes contacting a haloalkylmethoxysilane with an alcohol in the presence of a protic acid to form a haloalkylalkoxysilane. The haloalkylalkoxysilane is contacted with an iodide to form the iodoalkylalkoxysilane.

In accordance with another aspect of the present exemplary embodiment, a method for preparation of an iodoalkylalkoxysilane is provided. The iodoalkylalkoxysilane is of a general formula:

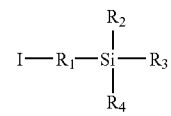

where $R_1$ is an alkyl group. At least one of $R_2$, $R_3$, and $R_4$ is an alkoxy group. Those of $R_2$, $R_3$, and $R_4$ which are not alkoxy groups, independently are selected from aliphatic and aromatic groups. The method includes substituting methoxy groups of a haloalkylmethoxysilane with alkoxy groups. The haloalkylmethoxysilane has a general formula:

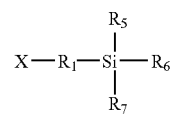

where X is selected from F, Cl, and Br. At least one of $R_5$, $R_6$, and $R_7$ is a methoxy group. Those of $R_5$, $R_6$, and $R_7$ which are not methoxy groups, independently are as for $R_2$, $R_3$, $R_4$ which are not alkoxy groups. The method further includes substituting the X group in the haloalkylalkoxysilane thus formed with an iodo group to form the iodoalkylalkoxysilane.

These and other non-limiting aspects and/or objects of the disclosure are more particularly discussed below.

BRIEF DESCRIPTION OF THE DRAWINGS

The following is a brief description of the drawings, which are presented for the purposes of illustrating the disclosure set forth herein and not for the purposes of limiting the same.

DETAILED DESCRIPTION

Figure 1:
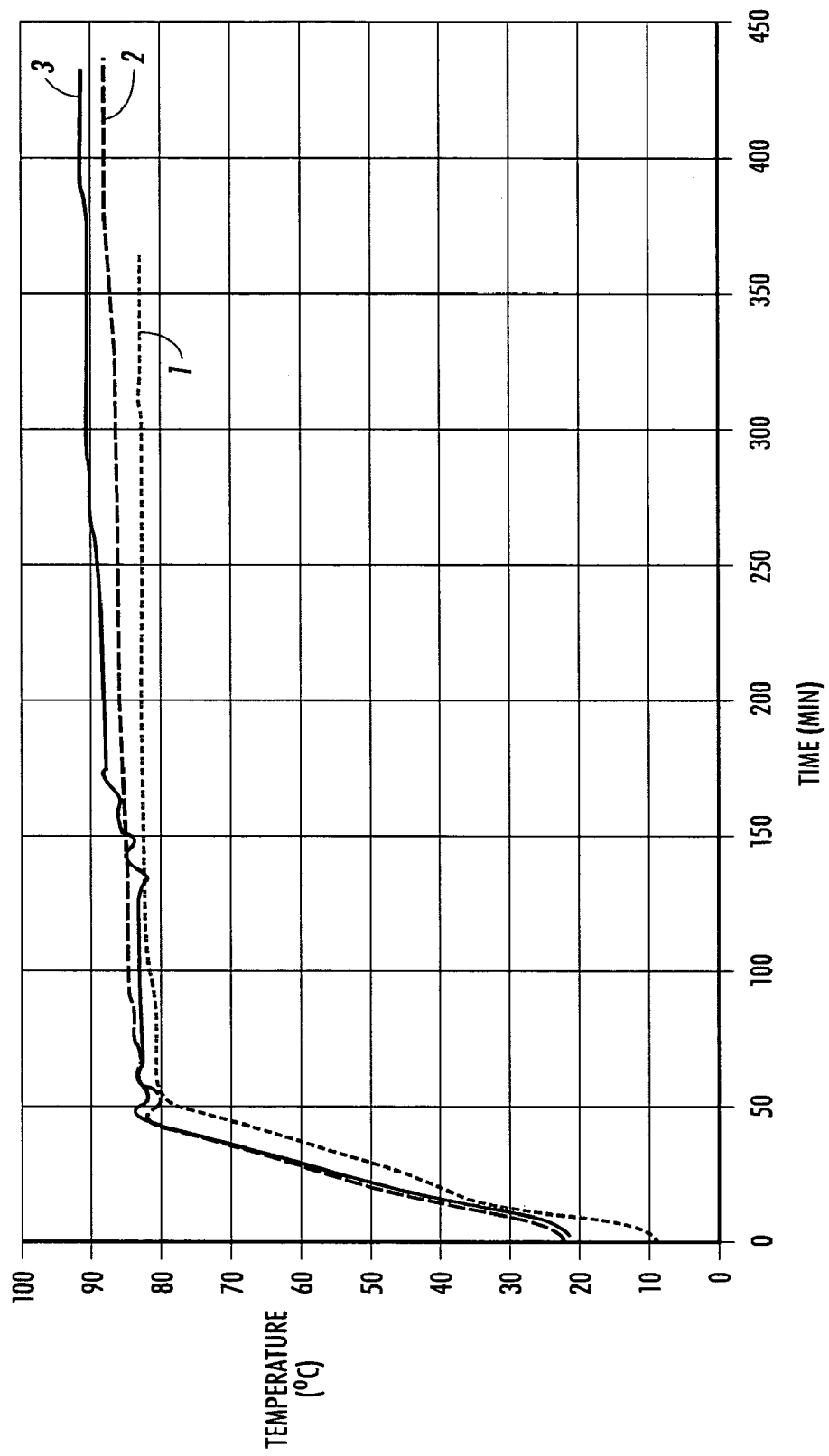
FIG. 1 is a plot of temperature vs. time for an isopropyl exchange reaction of 3-chloropropylmethyldimethoxysilane, where three successive isopropyl alcohol treatments are labeled 1, 2, and 3.

A method for preparation of an iodoalkylalkoxysilane, such as 3-iodopropylmethyidimethoxysilane, from a haloalkylmethoxysilane, such as 3-chloropropylmethyldimethoxysilane, includes contacting the haloalkylmethoxysilane with an alcohol in the presence of a protic acid to form a haloalkylalkoxysilane. In this step, the methoxy groups are replaced with alkoxy groups corresponding to the alcohol selected. The haloalkylalkoxysilane formed may be contacted with an iodide in a suitable organic solvent to form the iodoalkylalkoxysilane. Among other characteristics, the method allows preparation of 3-iodopropylmethyldimethoxysilane in a much shorter time than has been previously possible. The catalyst is less toxic than that which has been previously used. By avoiding the use of a silylchloride, the method enables an iodoalkylalkoxysilane to be formed without the need to scavenge hydrogen chloride. The method also results in a product having a high chemical purity.

The method will be described with particular reference to the conversion of 3-chloropropylmethyldimethoxysilane to 3-iodopropylmethyldiisopropoxysilanec. An exemplary overall reaction scheme is illustrated below:

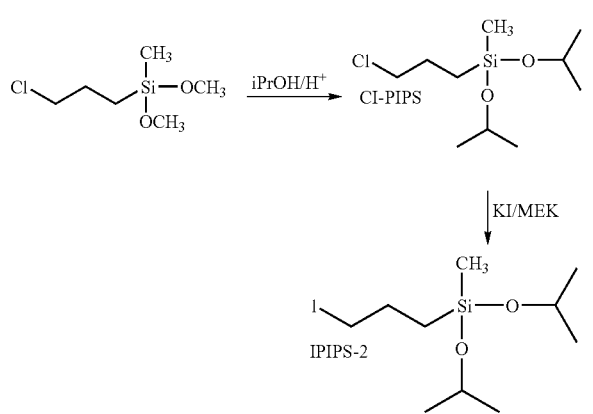

The iodoalkylalkoxysilane can have the general Formula A:

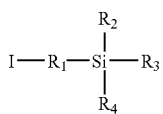

where $R_1$ is an alkyl group, which may be substituted or unsubstituted, such as a $C_2$-$C_{18}$ alkyl group, e.g., methyl, ethyl, propyl, and the like;

at least one of $R_2$, $R_3$, and $R_4$ is an alkoxy group, for example, the alkoxy group may be a $C_2$-$C_{18}$ alkoxy group, such as a methoxy, ethoxy, propoxy, or butoxy group. In one embodiment $R_3$ and $R_4$ are both an alkoxy group selected from $C_2$-$C_8$ alkoxy groups; and where those of $R_2$, $R_3$, and $R_4$ which are not alkoxy groups, independently are selected from aliphatic and aromatic groups, such as $C_1$-$C_8$ alkyl groups, such as methyl, ethyl, propyl, and butyl.

In one embodiment, $R_1$ is an n-propyl group, at least one of $R_2$, $R_3$, and $R_4$ is a propoxy group, and at least one of $R_2$, $R_3$, and $R_4$ is a $C_1$-$C_3$ alkyl group, such as a methyl group. In one embodiment, $R_3$ and $R_4$ are both alkoxy groups.

In one specific embodiment, the iodoalkylalkoxysilane is 3-iodopropylmethyldiisopropoxysilane, which has the formula:

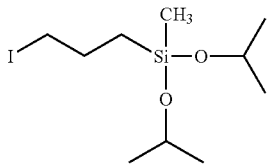

The haloalkylmethoxysilane can have the general Formula B, as follows:

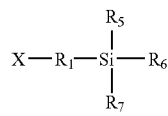

where X can be F, Cl, or Br;

$R_1$ is the same as in Formula A above;

at least one of $R_5$, $R_6$, and $R_7$ is a methoxy group; and those of $R_5$, $R_6$, and $R_7$ which are not methoxy groups, independently are as for $R_2$, $R_3$, $R_4$ which are not alkoxy groups in Formula A above.

In one specific embodiment, the haloalkylmethoxysilane is 3-chloropropyl-methyldimethoxysilane, which has the formula:

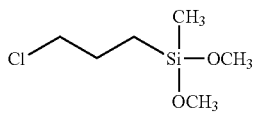

The reaction proceeds in two steps. The first step involves the conversion of the haloalkylmethoxysilane to the corresponding haloalkylalkoxysilane by substitution of all or substantially all of the methoxy groups with alkoxy groups other than methoxy groups. The substitution reaction involves contacting the haloalkylmethoxysilane with an alcohol in the presence of a protic acid at a suitable temperature and for sufficient time for the methoxy groups a haloalkylmethoxysilane to be replaced with alkoxy groups corresponding to the alcohol selected. The process is driven by fractional distillation of the produced methanol from the alcohol used to effect the transformation. In an exemplary embodiment, 3-chloropropyl-methyidimethoxysilane is reacted with isopropanol in the presence of a protic acid, such as p-toluenesulfonic acid (p-TSA). The reaction product is then converted to 3-iodopropylmethyidimethoxysilane in a second step by substitution of halo groups with iodo groups.

The alcohol can be a $C_2$-$C_{18}$ alcohol, such as a $C_3$-$C_8$ alcohol. In one embodiment, the alcohol is a secondary alcohol, selected from isopropanol (propan-2-ol), sec-butanol (butan-2-ol), iso-butanol (3-methyl-propan-1-ol), tert-butanol (2-methyl-propan-2-ol) and higher analogs containing $C_5$ to $C_{18}$, and combinations thereof. In one embodiment, the alcohol has a greater number of carbon atoms than in the alkoxy groups which it is to replace.

The protic acid can be an organic acid, such as p-toluenesulfonic acid (p-TSA), trifluoromethanesulfonic acid, chlorosulfonic acid, trichloroacetic acid, trifluoracetic acid, acetic acid, propionic acid or the like. In one embodiment, the boiling point of such organic acid is lower than the boiling point of the alcohol used in the process. The organic acid can be selected so as to avoid formation of an azeotropic mixture with the alcohol used in the process. The protic acid may also be an inorganic acid, such as sulfuric acid, phosphoric acid, or nitric acid, or an anhydrous acid such as hydrogen chloride, hydrogen bromide, or hydrogen iodide or a solid supported protic acid catalyst, such as Amberlyst® H15, or the like. Combinations of two or more protic acids may be employed.

The mixing ratio of the haloalkylmethoxysilane to the alcohol can be selected such that all or substantially all methoxy groups are converted to an alkoxy (e.g., propoxy) group. In one embodiment, 4 parts by weight of 3-chloropropyldimethoxymethylsilane is treated 3 times with 7.5 parts by weight isopropyl alcohol in such a way as to remove by fractional distillation the produced methyl alcohol along with some isopropyl alcohol and in such a way as to replace the distilled volume with equal volumes of isopropyl alcohol as the treatment progresses. In this embodiment, the treatment of 3-chloropropyldimethoxy-methylsilane with isopropyl alcohol is catalyzed by the presence, during the entire treatment, of about 0.01 parts by weight of paratoluenesulfonic acid hydrate. In one embodiment, a reaction temperature is maintained such that the fractional distillation of the mixture of methyl and isopropyl alcohols occurs at a rate of about 0.5 mL/min.

The reaction steps are optionally carried out in an inert atmosphere, such as argon or nitrogen.

In one embodiment, the alcohol is added stepwise, followed by a distillation step in which methanol generated in the reaction is distilled off. In this embodiment, no isopropyl alcohol need be added to the reaction vessel as the treatment progresses. Stepwise addition results in an increase in the purity of the reaction product. By employing three or more, more preferably, four or more such steps, a conversion of over 90% of the starting material to haloalkylalkoxysilane can be achieved. In one embodiment, the conversion is over 99%. At the end of the conversion step, any remaining volatile materials, such as isopropyl alcohol and methyl alcohol, may be distilled off by heating the reaction products to a suitable temperature. Optionally, purification of the haloalkylalkoxysilane is carried out. However, given the purity levels which can be achieved, further purification is generally not necessary.

The second step involves the replacement of the halo group (e.g., chloro) with an iodo group. One suitable process for the conversion of haloalkylalkoxysilane to iodoalkylalkoxysilane is by reaction with 1.0-4.0 equivalents of an alkali metal iodide in the presence of a suitable solvent, such as methylethylketone (MEK), acetone, methylisobutylketone (MIBK), combinations of such solvents, or the like, or the like, at a temperature of 80-90° C. (to maintain a gentle reflux, for which the temperature is adjusted depending on the choice of solvent) for 8-20 hours (referred to as a Finklestein reaction). As the alkali metal iodide, sodium or potassium iodide can be used. Potassium iodide has been found to decrease the reaction time needed for the conversion over that which can be achieved with sodium iodide. The conversion is accomplished in high yields with primary alkyl chlorides and bromides, such as the 3-chloropropyl group of the haloalkylalkoxysilane intermediate. The conversion can be monitored with gas chromatography (GC) to determine an appropriate reaction time. After cooling the reaction products, any insoluble salt present can be removed by filtration prior to concentrating the resulting solution, for example, by vacuum distillation. The resulting iodoalkylalkoxysilane can have a slight color of iodine. This coloration can be removed by treatment with 0.1-0.5 wt. equivalents of $Al_2O_3$ powder at room temperature for about 15 minutes, followed by filtration.

This method of producing 3-iodopropylmethyidiisopropoxysilane has advantages of cost over the use of 3-chloropropyidichloromethylsilane as a starting material. It has the added advantage of eliminating the need for an acid scavenger (whether in situ or online scavenger) to remove the hydrogen chloride that would be produced by reaction of 3-chloropropyldichloromethylsilane with isopropyl alcohol.

The haloalkylmethoxysilane used as the starting material (e.g., 3-chloropropylmethyldimethoxysilane) can be commercially purchased or can be produced by a hydrosilylation reaction of an appropriate substituted hydrosilane with an appropriate substituted alkyne. For example, 3-chloropropyldimethoxy-methylsilane can be produced by hydrosilylation of allylchloride with dichloro-methylsilane followed by treatment with methyl alcohol.

The iodoalkylalkoxysilane produced finds use as a chemical intermediate to produce functional aryl amine molecules which have application in the formation of thin films for photoreceptors. For example, the preparation of triarylamine hole transport molecules is optionally carried out by reaction of each of two carbonic acid salt groups on a triaryl amine precursor molecule with iodoalkylalkoxysilane resulting in elimination of hydrogen iodide salt. The reaction of the precursor molecule may be carried out in a suitable solvent, such as N,N-dimethylformamide (DMF) and toluene, in the presence of potassium carbonate, as follows:

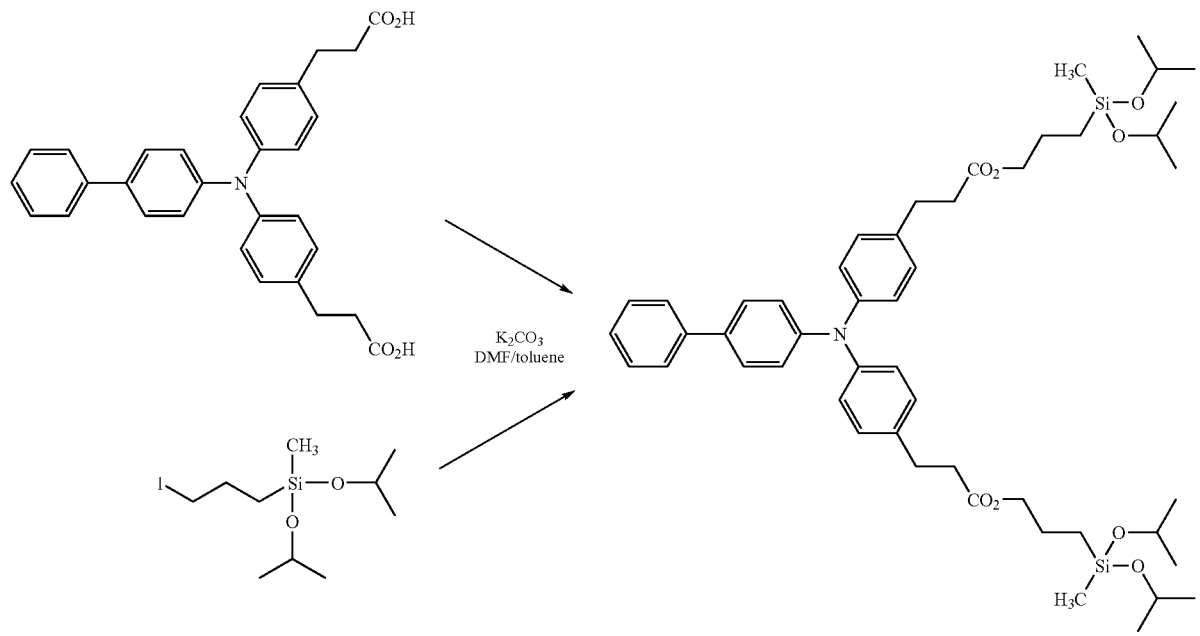

The siloxane containing triarylamine hole transport molecule thus produced can be chemically crosslinked, for example, with a siloxane containing binder material, such as 1,6-(dimethoxylmethylsilyl)hexane and water in the presence of a catalyst which on solution coating and thermal curing forms a siloxane overcoat. The overcoat may be used to protect an OPC (organic photoconductor) photosensitive material of a photoreceptor or other imaging member. For example, the overcoat components are laid down as a thin layer of approximately 3-5 μm in thickness over a charge transport layer of the photoreceptor and allowed to crosslink. The charge transport layer, and optionally other layers of the photoreceptor, such a supporting substrate and a photogenerating layer, may be formed by the processes described in U.S. Pat. No. 6,495,300 (Qi, et al.), U.S. Pat. No. 5,681,679 (Schank, et al.), or U.S. Pat. No. 5,368,967 (Schank. et. al.), which are incorporated herein by reference in their entireties.

The overcoat layer formed by the present process has been found to increase the mechanical life of an OPC by as much as ten fold. An imaging member incorporating the overcoat layer may be utilized in an imaging process including forming an electrostatic latent image on the imaging member, depositing toner particles on the imaging member in conformance with the latent image to form a toner image, and transferring the toner image to a receiving member. Additionally, the imaging member has more stable long term xerographic cycling and better image forming properties than the prior art.

In this regard, electrostatographic imaging systems, involve the formation and development of electrostatic latent images on an imaging surface of an electrostatographic or photoreceptor. Xerographic photoreceptors can be prepared in either a single-layer or a multilayer configuration. Depending on the application, the photoreceptors can be prepared in several forms, such as flexible belts, cylindrical drums, plates, etc. Belts are usually prepared on polymer substrates, poly(ethylene terephthalate) being the most common. For drums, the substrate is typically a metal cylinder. Usually, hollow aluminum cylinders are widely used in low- and mid-volume applications. The drum configuration, however, has certain process limitations for high-volume and color applications.

Photoreceptors are prepared by the sequential application of various layers (i.e., charge generating layer, charge transport layer, etc.) onto the outer surface of a polymer or drum substrate. Many coating techniques (i.e., spraying, spinning, extrusion, dipping, blade coating, roll coating, etc.) may be utilized to produce these layer(s). Vapor deposition may also be used for metallization and application of some pigments.

Most layers are coated from solutions or dispersions in organic solvents which produce solvent vapors. The choice of solvent is determined by such factors as materials solubility, evaporation rates, surface tension, toxicity, and environmental regulations. Commonly used solvent classes are alcohols, aromatics, esters, ethers, ketones, and nitrites. Because rapid solvent evaporation rates are desirable, low boiling solvents are preferred. Nevertheless, high boiling solvents such as toluene can be successfully used for some applications. In special cases, aqueous solutions or dispersions can also be used.

Electrostatographic flexible belt imaging member may be prepared by various techniques. A typical flexible supporting substrate is provided with an electrically conductive surface. For electrophotographic imaging members, at least one photoconductive layer is then applied to the electrically conductive surface. A hole or electron blocking layer may be applied to the electrically conductive surface prior to the application of the photoconductive layer. If desired, an adhesive layer may be utilized between the hole or electron blocking layer and the photoconductive layer. For multilayered photoreceptors, a charge generation layer is usually applied onto the hole or electron blocking layer and a charge transport layer is subsequently coated over the charge generation layer. For ionographic imaging members, an electrically insulating dielectric layer is applied directly onto the electrically conductive surface.

The supporting substrate may be opaque or substantially transparent and may comprise numerous materials having the required mechanical properties. Accordingly, the substrate may comprise a layer of an electrically non-conductive or conductive material such as an inorganic or an organic composition. As electrically non-conducting materials there may be employed various thermoplastic resins known for this purpose including polyesters, polycarbonates, polyamides, polyurethanes, and the like which are flexible in thin webs. The electrically insulating or conductive substrate should be flexible and in the form of an endless flexible belt. Preferably, the endless flexible belt shaped substrate comprises a commercially available biaxially oriented polyester.

The thickness of the supporting substrate layer depends on numerous factors, including beam strength, mechanical toughness, and economical considerations. Thus, the substrate layer used for a flexible belt application may be of substantial thickness, for example, about 150 micrometers, or of a minimum thickness of about 50 micrometers, provided that it produces no adverse effects on the belt. Preferably, the thickness of the substrate layer is between about 75 micrometers and about 100 micrometers for optimum flexibility, beam rigidity, and minimum stretch during cycling.

Where a separate flexible conductive layer is employed, it may vary in thickness over substantially wide ranges depending on the optical transparency and degree of flexibility desired for the electrostatographic member. Accordingly, for a flexible electrophotographic imaging device, the thickness of the conductive layer may be between about 20 angstroms and about 750 angstroms, and more preferably between about 100 angstroms and about 200 angstroms for an optimum combination of electrical conductivity, flexibility and light transmission. The flexible conductive layer may be an electrically conductive metal layer formed, for example, on the substrate by any suitable coating technique, such as a vacuum depositing technique. Typical metals include aluminum, copper, gold, zirconium, niobium, tantalum, vanadium and hafnium, titanium, nickel, stainless steel, chromium, tungsten, molybdenum, and the like. Regardless of the technique employed to form the metal layer, a thin layer of metal oxide forms on the outer surface of most metals upon exposure to air. Thus, when other layers overlying the metal layer are characterized as "contiguous" layers, it is intended that these overlying contiguous layers may, in fact, contain a thin metal oxide layer that has formed on the outer surface of an oxidizable metal layer. A typical electrical conductivity for conductive layers for electrophotographic imaging members in slow speed copiers is about $10^{-2}$ to $10^{-3}$ per ohms/square.

After formation of an electrically conductive surface, a hole blocking or electron blocking layer, hereinafter referred to as a charge blocking layer, may be applied thereto for photoreceptors. Generally, electron blocking layers for positively charged photoreceptors allow holes from the imaging surface of the photoreceptor to migrate toward the conductive layer and hole blocking layers for negatively charged photoreceptors allow electrons from the imaging surface of the photoreceptor to migrate toward the conductive layer. Any suitable charge blocking layer capable of forming an electronic barrier to holes or electrons between the adjacent photoconductive layer and the underlying conductive layer may be utilized. The charge blocking layer may be applied by any suitable conventional technique such as spraying, dip coating, draw bar coating, gravure coating, silk screening, air knife coating, reverse roll coating, vacuum deposition, chemical treatment and the like. The charge blocking layer should be continuous and have a dry thickness of less than about 0.2 micrometer.

An adhesive layer is usually applied to the charge blocking layer. Any suitable adhesive layer well known in the art may be utilized. Typical adhesive layer materials include, for example, polyesters, polyurethanes, and the like. Satisfactory results may be achieved with the adhesive layer thickness between about 0.05 micrometer and about 0.3 micrometer. Conventional techniques for applying an adhesive layer coating mixture to the charge blocking layer include spraying, dip coating, roll coating, wire wound rod coating, gravure coating, Bird applicator coating, and the like. Drying of the deposited coating may be effected by any suitable conventional technique such as oven drying, infra red radiation drying, air drying and the like.

Any suitable charge generating (photogenerating) layer may be applied onto the adhesive layer. Charge generating layers are well know in the art and can comprise homogeneous layers or photoconductive particles dispersed in a film forming binder. Examples of charge generating layers are described, for example, in U.S. Pat. No. 3,357,989, U.S. Pat. No. 3,442,781, and U.S. Pat. No. 4,415,639, the disclosures thereof being incorporated herein in their entirety. Other suitable photogenerating materials known in the art may also be utilized, if desired.

Any suitable polymeric film forming binder material may be employed as the matrix in of the photogenerating layer. Typical polymeric film forming materials include those described, for example, in U.S. Pat. No. 3,121,006, the disclosure thereof being incorporated herein in its entirety. The photogenerating composition or pigment may be present in the film forming binder composition in various amounts. Generally, from about 5 percent by volume to about 90 percent by volume of the photogenerating pigment is dispersed in about 10 percent by volume to about 90 percent by volume of the resinous binder. Preferably from about 20 percent by volume to about 30 percent by volume of the photogenerating pigment is dispersed in about 70 percent by volume to about 80 percent by volume of the resinous binder composition.

The photogenerating layer generally ranges in thickness from about 0.1 micrometer to about 5 micrometers, and more preferably from about 0.3 micrometer to about 3 micrometers. The photogenerating layer thickness is related to binder content. Higher binder content compositions generally require thicker layers for photogeneration.

Any suitable and conventional technique may be utilized to mix and thereafter apply the photogenerating layer coating mixture to the previously dried adhesive layer. Drying of the deposited coating may be effected by any suitable conventional technique.

The charge transport layer may comprise any suitable transparent organic polymer or non-polymeric material capable of supporting the injection of photogenerated holes or electrons from the charge generating layer and allowing the transport of these holes or electrons through the organic layer to selectively discharge the surface charge. The charge transport layer not only serves to transport holes or electrons, but also protects the photoconductive layer from abrasion or chemical attack. The charge transport layer should exhibit negligible, if any, discharge when exposed to a wavelength of light useful in xerography, e.g. 4000 Angstroms to 9000 Angstroms. The charge transport layer is normally transparent in a wavelength region in which the electrophotographic imaging member is to be used when exposure is effected therethrough to ensure that most of the incident radiation is utilized by the underlying charge generating layer. When used with a transparent substrate, imagewise exposure or erase may be accomplished through the substrate with all light passing through the substrate. In this case, the charge transport material need not transmit light in the wavelength region of use if the charge generating layer is sandwiched between the substrate and the charge transport layer. The charge transport layer in conjunction with the charge generating layer is an insulator to the extent that an electrostatic charge placed on the charge transport layer is not conducted in the absence of illumination. Charge transport layer materials are well known in the art.

The charge transport layer may comprise activating compounds or charge transport molecules dispersed in normally electrically inactive film forming polymeric materials. These charge transport molecules may be added to polymeric materials which are incapable of supporting the injection of photogenerated holes and incapable of allowing the transport of these holes. An especially preferred charge transport layer employed in multilayer photoconductors comprises from about 25 percent to about 75 percent by weight of at least one charge transporting aromatic amine, and about 75 percent to about 25 percent by weight of a polymeric film forming resin in which the aromatic amine is soluble. Examples of typical charge transporting aromatic amines include triphenylmethane, bis(4-diethylamine-2-methylphenyl)phenylmethane; 4'4"-bis(diethylamino)-2',2"-dimethyltriphenyl-methane; N,N'-bis(alkylphenyl)-(1,1'-biphenyl)-4,4'-diamine wherein the alkyl is, for example, methyl, ethyl, propyl, n-butyl, etc.; N,N'-diphenyl-N,N'-bis(3"-methylphenyl)-(1,1'biphenyl)-4,4'diamine; and the like, dispersed in an inactive resin binder.

Any suitable inactive thermoplastic resin binder may be employed. Typical inactive resin binders include polycarbonate resins, polyvinylcarbazole, polyester, polyarylate, polyacrylate, polyether, polysulfone, and the like. Molecular weights can vary from about 20,000 to about 150,000.

The thickness of the charge transport layer may range from about 10 micrometers to about 50 micrometers, and preferably from about 20 micrometers to about 35 micrometers. Optimum thicknesses may range from about 23 micrometers to about 31 micrometers.

An optional conventional ground strip may be utilized along one edge of the electrophotographic imaging member. The ground strip may comprise a film forming polymer binder and electrically conductive particles. The ground strip may comprise materials such as those enumerated in U.S. Pat. No. 4,664,995. The ground strip layer may have a thickness from about 7 micrometers to about 42 micrometers, and preferably from about 14 micrometers to about 23 micrometers.

An optional conventional anti-curl layer may also be employed. The anti-curl layer may comprise thermoplastic organic polymers or inorganic polymers that are electrically insulating or slightly semi-conductive. The anti-curl layer provides flatness and/or abrasion resistance and may also contain microcrystalline silica or organic particulates to improve its frictional and wear properties. The anti-curl layer is formed at the back side of the substrate, opposite to the imaging layers. The thickness of the anti-curl layer is from about 3 micrometers to about 35 micrometers. An example of an anti-curl backing layer is described in U.S. Pat. No. 4,654,284, the entire disclosure of this patent being incorporated herein by reference.

The overcoat layer is formed using the 3-iodopropylmethyidiisopropoxy-silane produced by the present process. The overcoating layer may range in thickness from about 2 micrometers to about 8 micrometers, and preferably from about 3 micrometers to about 6 micrometers.

The above processes, compositions and materials can be utilized to produce a photoreceptor. The photoreceptors produced by the present disclosure can be utilized in an electrophotographic imaging process by, for example, first uniformly electrostatically charging the photoreceptor, then exposing the charged photoreceptor to a pattern of activating electromagnetic radiation such as light, which selectively dissipates the charge in the illuminated areas of the photoreceptor while leaving behind an electrostatic image in the non-illuminated areas. This electrostatic latent image may then be developed at one or more developing stations to form a visible image by depositing finely divided electroscopic toner particles, for examples, from a developer composition, on the surface of the photoreceptor. The resulting visible toner image can be transferred to a suitable receiving member, such as paper. The photoreceptor is then typically cleaned at a cleaning station prior to being recharged for formation of subsequent images.

The following examples describe exemplary embodiments of the present invention. These examples are merely illustrative, and in no way limit the present invention to the specific materials, conditions or process parameters set forth therein. All parts and percentages are by weight unless otherwise indicated.

EXAMPLES

Figure 2:
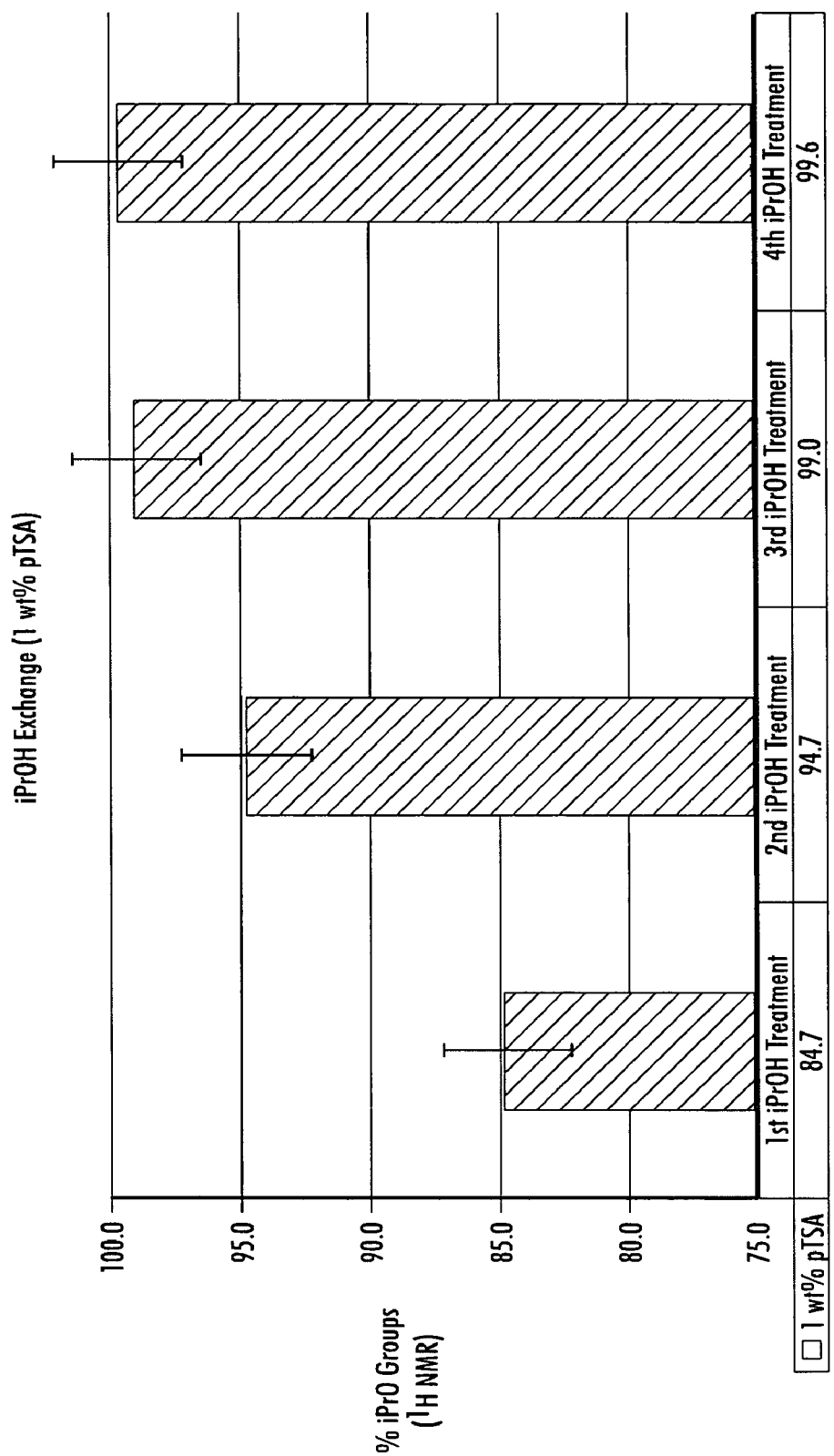
FIG. 2 is a bar graph showing the percentage of isopropoxy groups as a function of the number of isopropyl alcohol treatments, as measured by $^1$HNMR.

To a 2 L 3-necked flask fitted with dropping funnel, argon inlet, mechanical stirring and still head was charged in order 250 ml isopropyl alcohol (iPrOH), 4 g p-toluenesulfonic acid hydrate (p-TSA) (1% by weight), 400 mL of 3-chloropropylmethyldimethoxysilane and an additional 500 mL iPrOH. The contents were heated to gentle reflux 8 hours while iPrOH was added into the reaction at the same rate as distillation (total of about 500 mL in 8 hours). This was repeated for 2 additional 8 hour periods. The temperature profiles of each treatment are shown in FIG. 1. Finally the reaction was heated to 100° C. and any volatile materials were distilled (remaining iPrOH and MeOH). The purity of the material as a function of the number of treatments is shown in FIG. 2. The final material was shown to be 99.6% 3-chloropropylmethyidiisopropoxysilane. No further purification was performed as the trace of p-TSA does not affect the next step.

Figure 3:
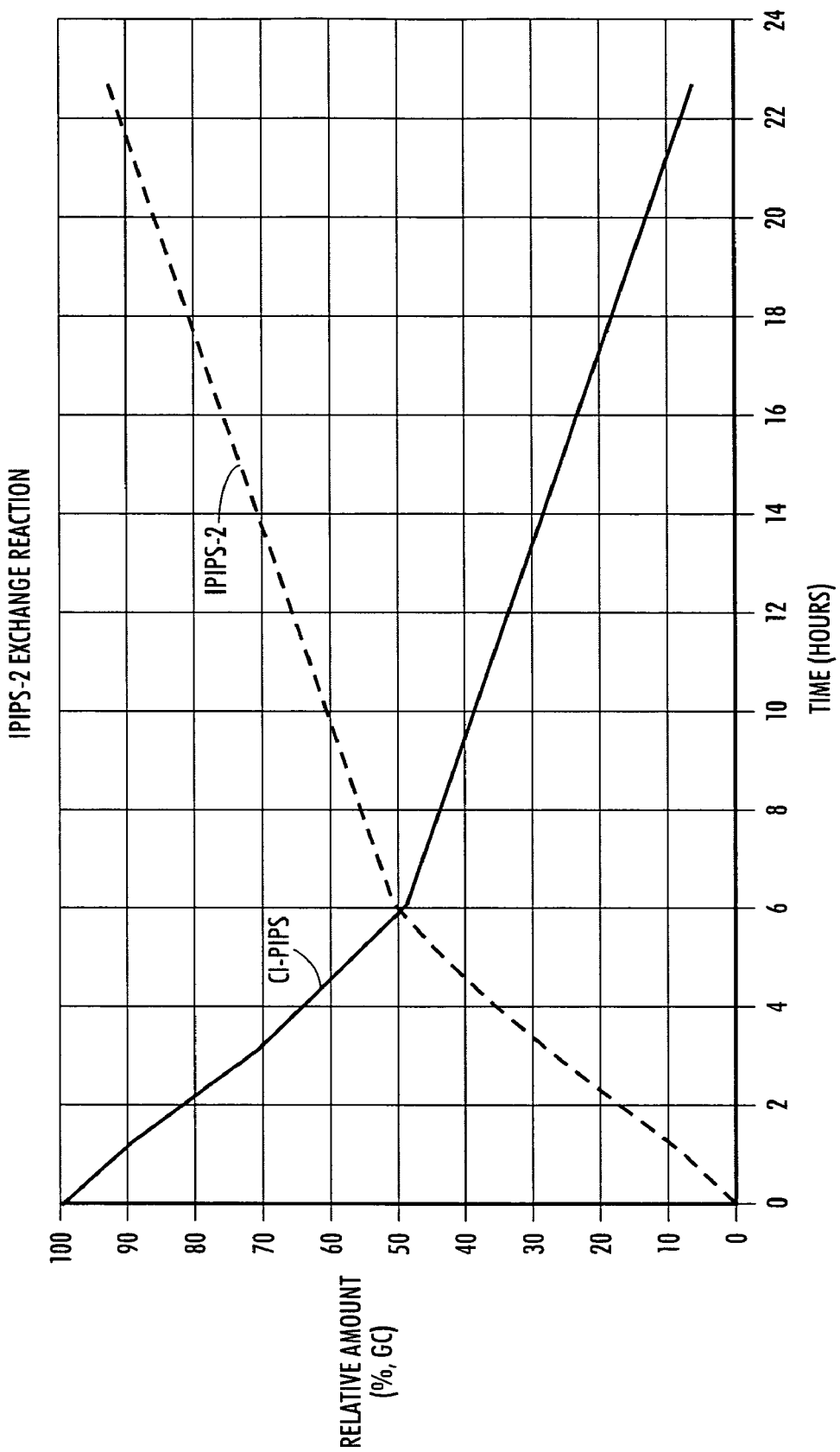
FIG. 3 is a plot showing relative amounts of 3-chloropropylmethyidiisopropoxysilane (CIPIPS) and 3-iodopropylmethyl-diisopropoxysilane (IPIPS 2) as a function of time during conversion of CIPIPS to IPIPS 2.

To a 2 L 3-necked flask fitted with mechanical stirring, argon inlet and reflux condenser was charged 200 mL of 3-chloropropylmethyidiisopropoxysilane (product from above), 600 mL methylethylketone (MEK) and 169.9 g (1.5 equivalents) sodium iodide. The mixture was heated at gentle reflux (83° C.) overnight. Monitoring of the reaction was done using GC and the conversion as a function of time is illustrated in FIG. 3. The reaction was cooled and filtered to remove insoluble salt before concentrating the solution. The concentrated solution was vacuum distilled to obtain pure IPIPS-2 (Table 1) with a slight color of iodine. The yield was 25.96%. Treatment of the IPIPS-2 with 1/5 wt. equiv. of $Al_2O_3$ (CG-20) at room temperature was sufficient to remove the color of iodine within 15 minutes.

TABLE 1

IPIPS-2 Distillation Procedure

| Fraction | Yield | Density (g/mL) | Purity ($^1$HNMR) | Decolorized with $Al_2O_3$* | Decomposition after Decolorization ($^1$HNMR) |
|---|---|---|---|---|---|
| 1 | 34.6 g (12.51%) | 1.2165 | 90.10% | No | No change |
| 2 | 46.42 g (16.78%) | 1.2046 | 94.30% | No | No change |
| 3 | 35.75 g (12.92%) | 1.2071 | 99+% | 5 min | No change |
| 4 | 36.06 g (13.04%) | 1.2177 | 99+% | overnight | No change |
| Total | 152.83 g (55.25%) | | | | |

*Decolorization with 0.2 g $Al_2O_3$ in 1.0 g fraction, with shaking overnight, removes the iodine color.

Further improvements can be made by changing the conditions under which the distillation is performed. For example, by reducing the volume of the headspace in the distillation apparatus, the overall yield is improved to 84% (from 3-chloropropyidimethoxymethylsilane) as illustrated in Table 2.

TABLE 2

IPIPS-2 Distillation Procedure

| Fraction | Yield | Density (g/mL) | Purity ($^1$H NMR) |
|---|---|---|---|
| 1 | 158.03 g (38.56%) | 1.4268 | 98% |
| 2 | 166.19 g (40.55%) | 1.4504 | 99+% |
| 3 | 21.9 g (5.34%) | 1.4499 | 99+% |
| Total | 346.12 g (84.45%) | | |

Reducing the volume of the headspace in the distillation apparatus allows for an improvement in the yield.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

The invention claimed is:

1. A method for preparation of an iodoalkylalkoxysilane comprising:
   contacting a haloalkylmethoxysilane with an alcohol in the presence of a protic acid to form a haloalkylalkoxysilane; and
   contacting the haloalkylalkoxysilane with an iodide to form the iodoalkylalkoxysilane.

2. The method of claim 1, wherein the alcohol is selected from the group consisting of $C_2$-$C_{18}$ alcohols, and combinations thereof.

3. The method of claim 2, wherein the alcohol is a primary alcohol.

4. The method of claim 2, wherein the alcohol is at least a $C_2$ alcohol.

5. The method of claim 4, wherein the alcohol includes isopropyl alcohol.

6. The method of claim 1, wherein the haloalkylmethoxysilane includes a halo group selected from bromo, chloro and combinations thereof.

7. The method of claim 1, wherein the iodoalkylalkoxysilane comprises 3-iodopropylmethyldimethoxysilane.

8. The method of claim 7, wherein the haloalkylmethoxysilane comprises 3-chloropropylmethyldimethoxysilane.

9. The method of claim 1, wherein the protic acid is selected from p-toluenesulfonic acid, trifluoromethanesulfonic acid, chlorosulfonic acid, trichloroacetic acid, trifluoracetic acid, acetic acid, propionic acid, sulfuric acid, phosphoric acid, nitric acid, an anhydrous acid, a solid supported protic acid catalyst, and combinations thereof.

10. The method of claim 1, wherein the iodide comprises an alkali metal iodide.

11. The method of claim 10, wherein the alkali metal iodide comprises potassium iodide.

12. The method of claim 1, wherein the step of contacting a haloalkylmethoxysilane with an alcohol occurs in an inert atmosphere.

13. The method of claim 1, wherein the step of contacting a haloalkylmethoxysilane with an alcohol includes stepwise addition of the alcohol.

14. The method of claim 1, wherein the step of contacting the haloalkylalkoxysilane with an iodide is carried out in a solvent.

15. The method of claim 14, wherein the solvent is selected from methylethylketone, acetone, methylisobutylketone, and combinations thereof.

16. A method of forming a triarylamine hole transport molecule comprising:
   preparation of an iodoalkylalkoxysilane by the method of claim 1;
   reacting the iodoalkylalkoxysilane with at least one carbonic acid group of a triaryl amine precursor molecule to form the triarylamine hole transport molecule.

17. The method of claim 16, wherein the step of reacting the iodoalkylalkoxysilane with at least one carbonic acid group is carried out in a solvent, in the presence of an alkali metal carbonate.

18. The method of claim 17, wherein the solvent comprises N, N-dimethylformamide and toluene.

19. The method of claim 1, wherein the iodoalkylalkoxysilane comprises 3-iodopropylmethyldiisopropoxysilane.

20. A method for preparation of an iodoalkylalkoxysilance of a general formula:

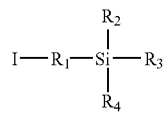

where $R_1$ is an alkyl group, $R_2$, $R_3$, and $R_4$ are independently selected from alkoxy, aliphatic, and aromatic groups, and at least one of $B_2$, $R_3$, and $R_4$ is an alkoxy group, comprising:

a) reacting a haloalkylmethoxysilane with an alcohol in the presence of a protic acid to form a haloalkylalkoxysilane, the haloalkylmethoxysilane having a general formula:

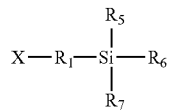

where X is selected from F, Cl, and Br; $R_5$, $R_6$, and $R_7$ are independently selected from methoxy, aliphatic, and aromatic groups, and at least one of $R_5$, $R_6$, and $R_7$ is a methoxy group; and the haloalkylalkoxysilane comprising at least one alkoxy group having the same number of carbon atoms as the alcohol; and b) substituting the X group in the haloalkylalkoxysilane formed in step a) with an iodo group to form the iodoalkylalkoxysilane.

* * * * *